US012691088B2

(12) United States Patent
Qiu et al.

(10) Patent No.: US 12,691,088 B2
(45) Date of Patent: Jul. 28, 2026

(54) REACTIVATION OF MTOR IN ACUTE KIDNEY INJURY (AKI)

(71) Applicant: The Trustees of Columbia University in the City of New York, New York, NY (US)

(72) Inventors: Andong Qiu, Bronx, NY (US); Andrew Beenken, New York, NY (US); Jonathan Barasch, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 433 days.

(21) Appl. No.: 18/223,810

(22) Filed: Jul. 19, 2023

(65) Prior Publication Data

US 2023/0364046 A1      Nov. 16, 2023

Related U.S. Application Data

(63) Continuation of application No. PCT/US2022/012762, filed on Jan. 18, 2022.

(60) Provisional application No. 63/144,751, filed on Feb. 2, 2021, provisional application No. 63/139,143, filed on Jan. 19, 2021.

(51) Int. Cl.
| | |
|---|---|
| A61K 31/198 | (2006.01) |
| A61K 9/00 | (2006.01) |
| A61K 31/4172 | (2006.01) |
| A61P 13/12 | (2006.01) |

(52) U.S. Cl.
CPC .......... *A61K 31/198* (2013.01); *A61K 9/0019* (2013.01); *A61K 31/4172* (2013.01); *A61P 13/12* (2018.01)

(58) Field of Classification Search
CPC ................................................ A61K 31/198
See application file for complete search history.

(56) References Cited

U.S. PATENT DOCUMENTS

| | | | |
|---|---|---|---|
| 7,910,566 | B2 | 3/2011 | Feinstein |
| 8,940,696 | B2 | 1/2015 | Szeto |
| 10,227,314 | B2 | 3/2019 | Duron |
| 2009/0011977 | A1 | 1/2009 | Hill et al. |
| 2016/0324930 | A1 | 11/2016 | Van Antwerp |
| 2018/0205366 | A1 | 7/2018 | Vesely et al. |

FOREIGN PATENT DOCUMENTS

| | | |
|---|---|---|
| WO | WO-2017147058 A1 | 8/2017 |
| WO | WO-2022/159382 A1 | 7/2022 |

OTHER PUBLICATIONS

Umber et al., Clinical Nephrology, 2014, 81(2):93-99.*
Xie et al., Chinese Journal of Traumatology, 2004, 7(2): 87-90.*
Kin et al., Transplantation Proceedings, 1996, 28(3):1889-1890.*
Bellomo, et al., "Acute kidney injury", The Lancet, 380:756-766, Aug. 25, 2012 (11 pages).
Clermont, et al., "Renal failure in the ICU: Comparison of the impact of acute renal failure and end-stage renal disease on ICU outcomes", Kidney International, 62:986-996, 2002 (11 pages).
Doig, et al., "Intravenous amino acid therapy for kidney function in critically ill patients: a randomized controlled trial", Intensive Care Med, DOI: 10. 1007/s00134-015-3827-9, available online Apr. 30, 2015 (12 pages).
Grahammer, et al., "mTOR Regulates Endocytosis and Nutrient Transport in Proximal Tubular Cells", J. Am. Soc. Nephrol., 28(1):230-241, Jan. 2017, published online Jun. 13, 2016 (15 pages).
International Search Report and Written Opinion issued by U.S. Patent and Trademark Office as International Searching Authority, in International Application No. PCT/US22/12762, dated Apr. 12, 2022 (16 pages).
Jiang, et al., "Autophagy in proximal tubules protects against acute kidney injury", Kidney International, 82:1271-1283, Dec. 2012, published online Aug. 1, 2012 (13 pages).
Jiang, et al., "Autophagy is a Renoprotective Mechanism During in Vitro Hypoxia and in Vivo Ischemia-Reperfusion Injury", American Journal of Pathology, 176(3):1181-1192, Mar. 2010 (12 pages).
Kelly, et al., "Minocycline inhibits apoptosis and inflammation in a rat model of ischemic renal injury", American Journal of Physiology Renal Physiology, 287(4):F760-F766, Oct. 2004, published online Jun. 1, 2004 (7 pages).
Leaf, et al., "Cathelicidin antimicrobial protein, vitamin D, and risk of death in critically ill patients", Critical Care, 19: 80, Mar. 10, 2015 (9 pages).
Mehr, et al., "De novo NAD+ biosynthetic impairment in acute kidney injury in humans", Author Manuscript published in Final edited form as Nature Medicine, 24(9):1351-1359, Sep. 2018 (27 pages).
Meng, et al., "Glutamine and asparagine activate mTORC1 independently of Rag GTPases", J. Biol Chem., 295(10):2890-2899, 2020 (10 pages).
Menshikh, et al., "Capillary rarefaction is more closely associated with CKD progression after cisplatin, rhabdomyolysis, and ischemia-reperfusion-induced AKI than renal fibrosis", American Journal of Physiology: Renal Physiology, 317(5):F1383-F1397, Nov. 1, 2019 (21 pages).
Simic, et al., "Nicotinamide riboside with pterostilbene (NRPT) increases NAD+ in patients with acute kidney injury (AKI): a randomized, double-blind, placebo-controlled, stepwise safety study of escalating doses of NRPT in patients with AKI", BMC Nephrology, 21:342, published online Aug. 13, 2020 (9 pages).

(Continued)

*Primary Examiner* — Rei Tsang Shiao
(74) *Attorney, Agent, or Firm* — Wilmer Cutler Pickering Hale and Dorr LLP

(57) ABSTRACT

The subject method described herein relates to a method of treating, preventing, or reducing the incidence of Acute Kidney Injury (AKI) in a subject in need thereof by administering to the subject a pharmaceutically effective amount of one or more amino acids.

21 Claims, 12 Drawing Sheets

(56)                References Cited

OTHER PUBLICATIONS

Sutton, et al., "Minocycline reduces renal microvascular leakage in a rat model of ischemic renal injury", American Journal of Physiology: Renal Physiology, 288(1):F91-F97, Jan. 2005, first published Sep. 7, 2004 (7 pages).

Zhou, et al., "Metabolic reprogramming by the S-nitroso-CoA Reductase system protects from kidney injury", Author Manuscript published in Final edited form as Nature, 565(7737):96-100, Jan. 2019 (35 pages).

* cited by examiner

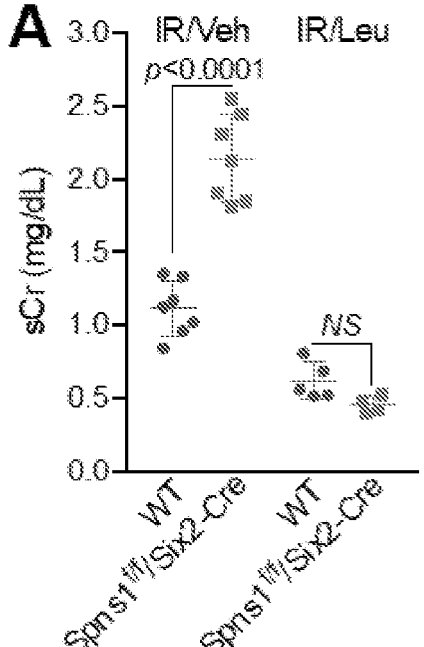
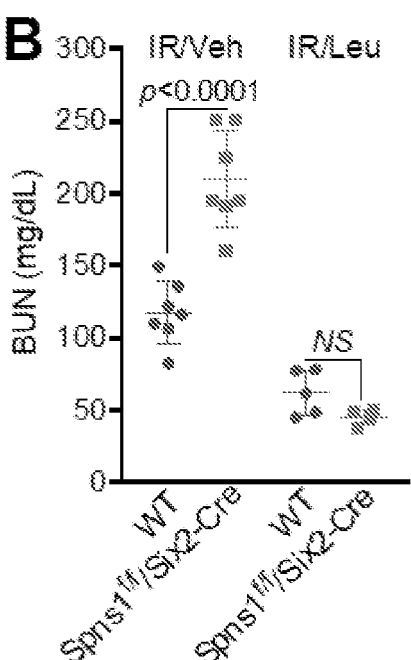
FIGS. 1A-B

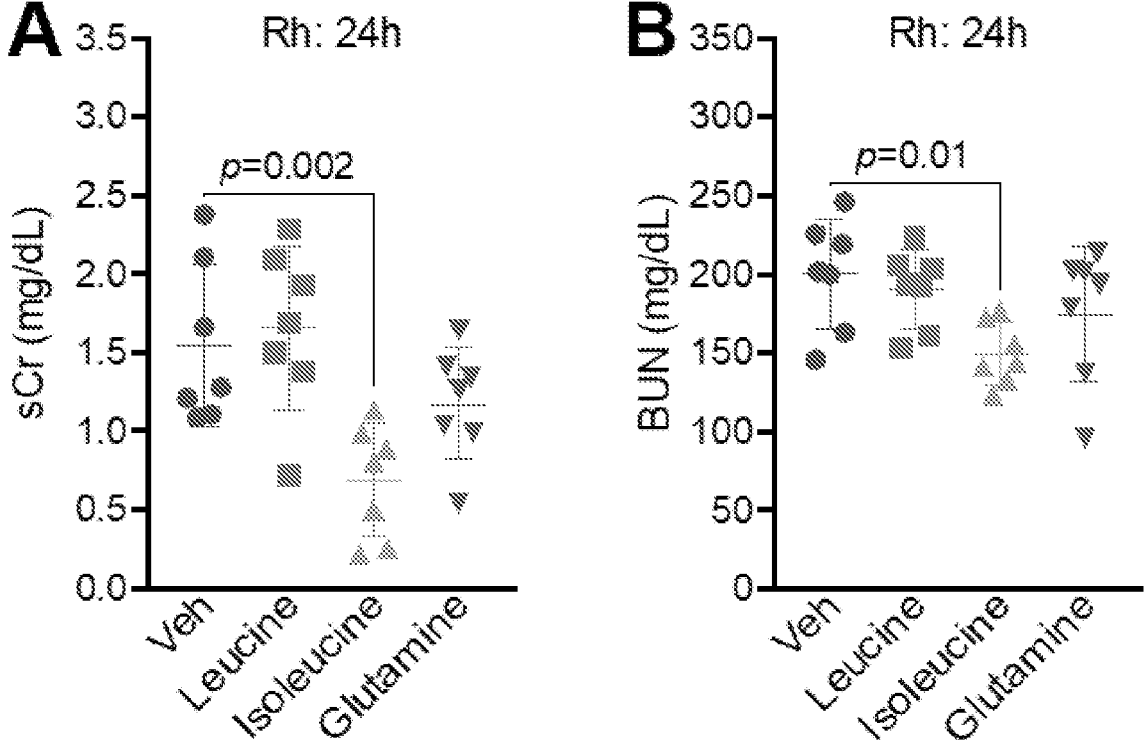
FIGS. 2A-B

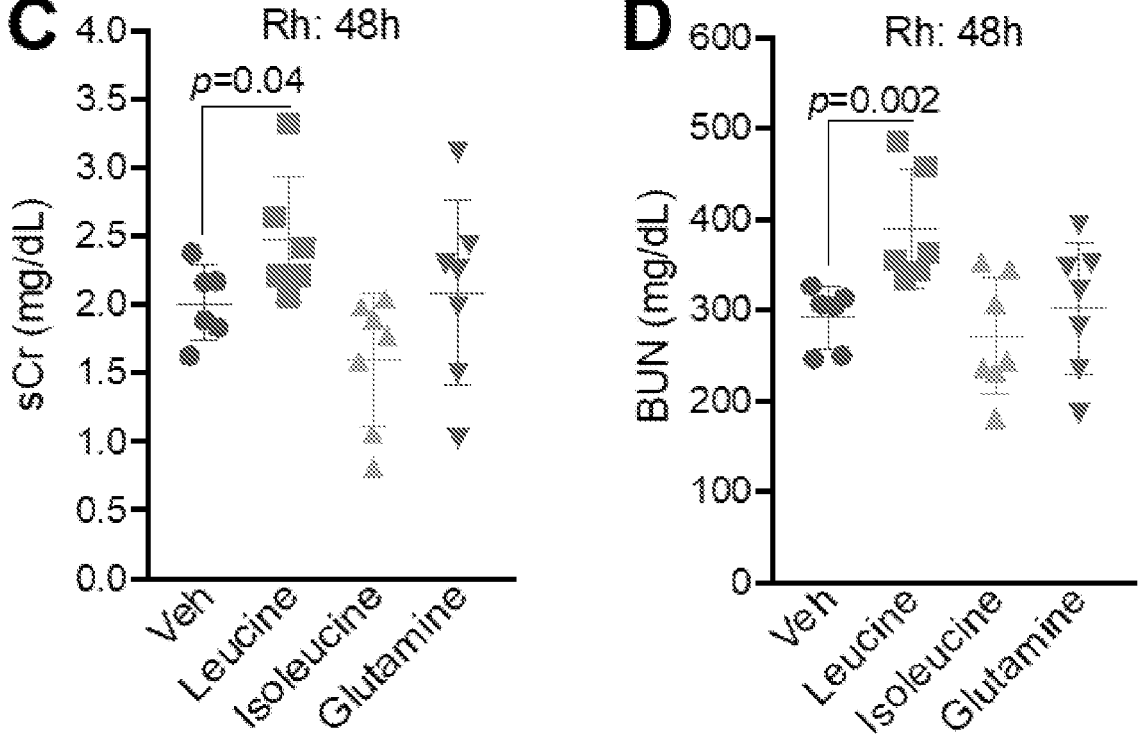
FIGS. 2C-D

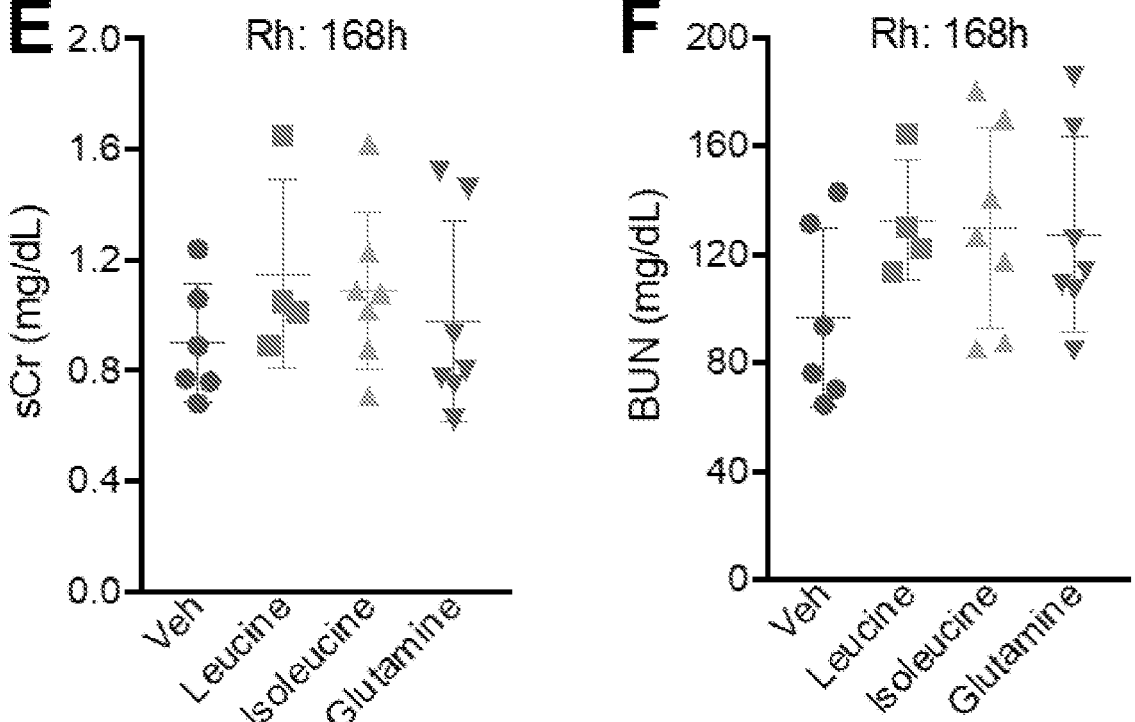
FIGS. 2E-F

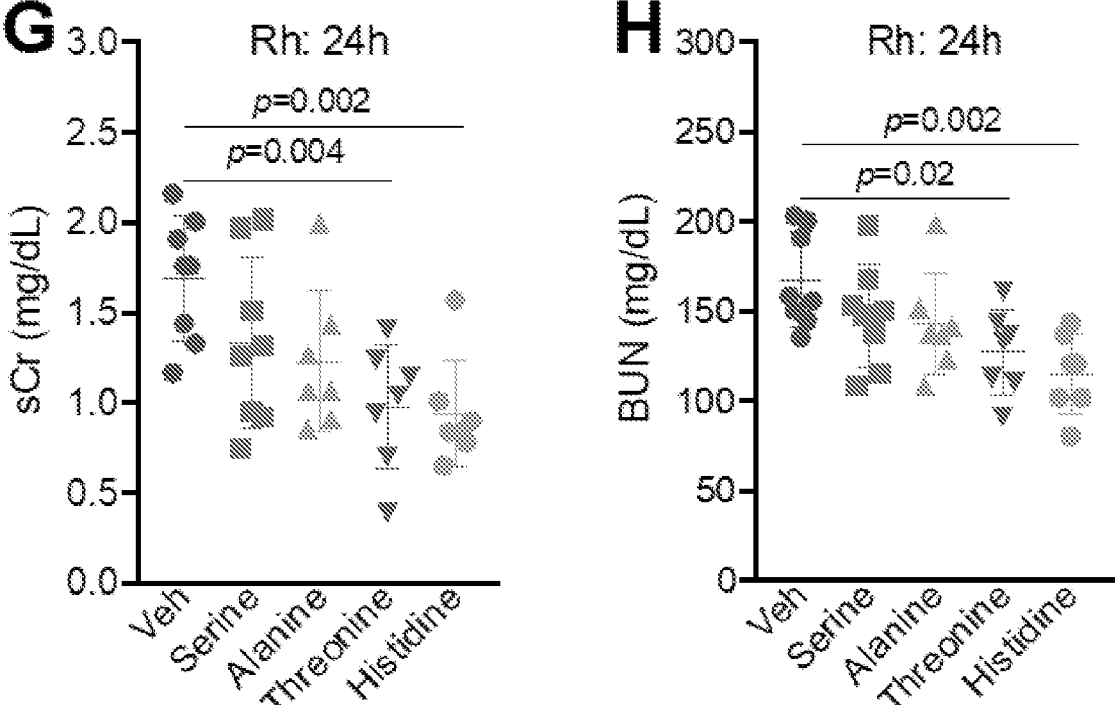
FIGS. 2G-H

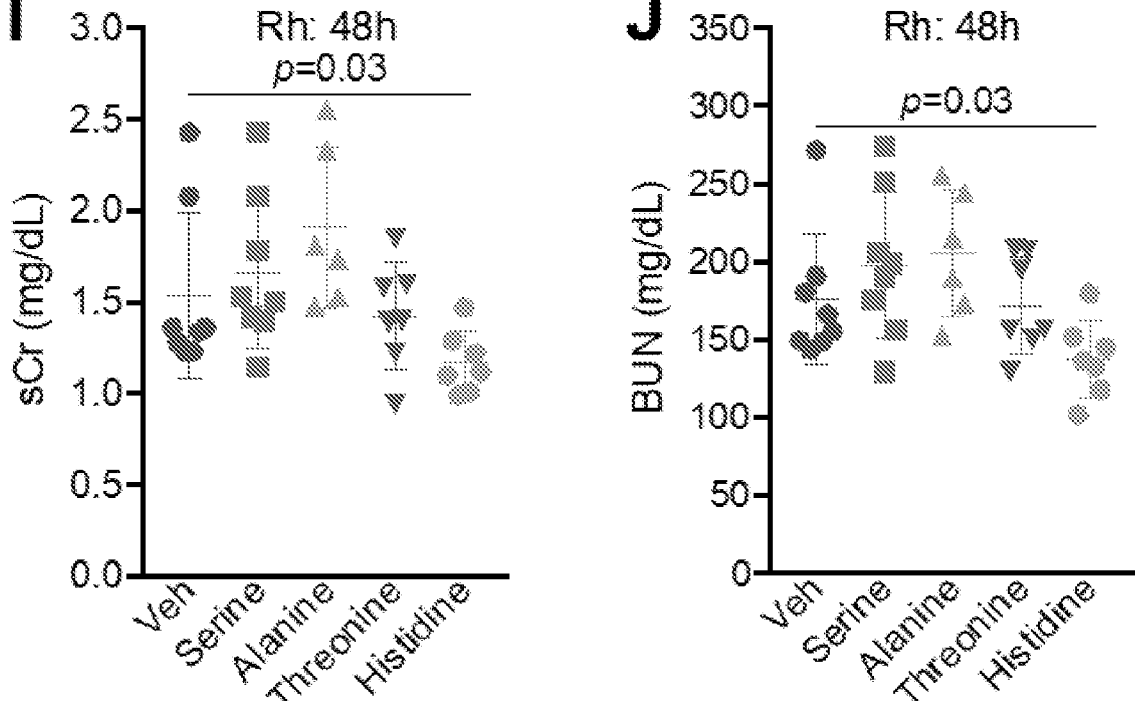
FIGS. 2I-J

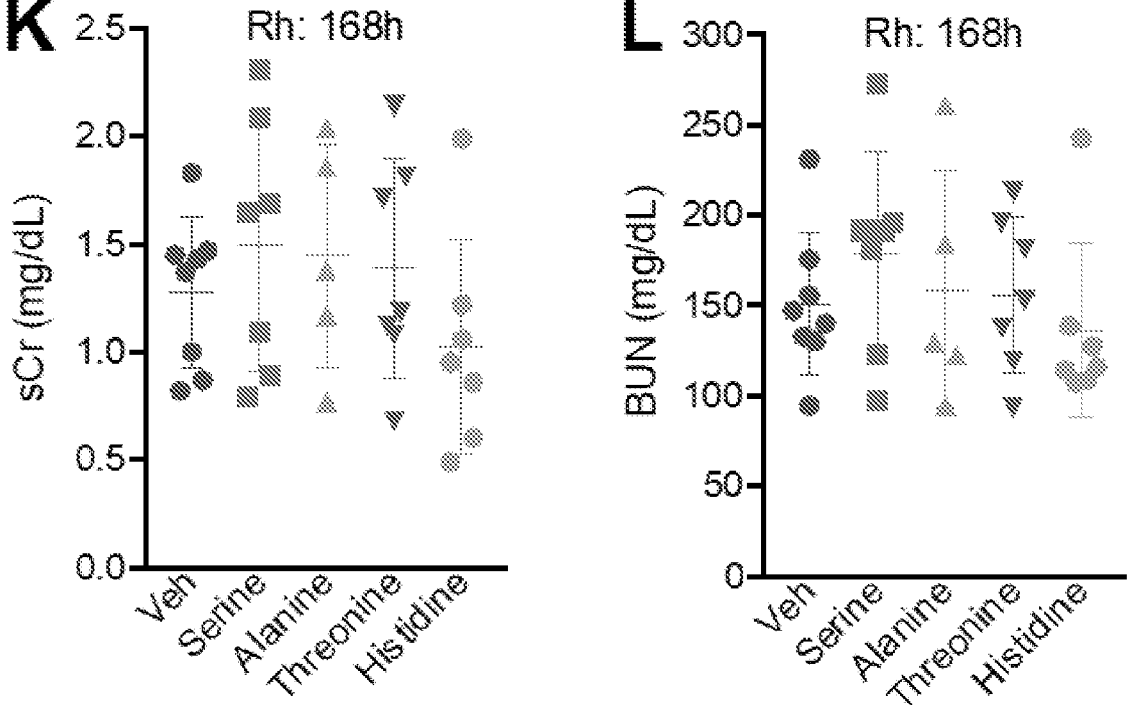
FIGS. 2K-L

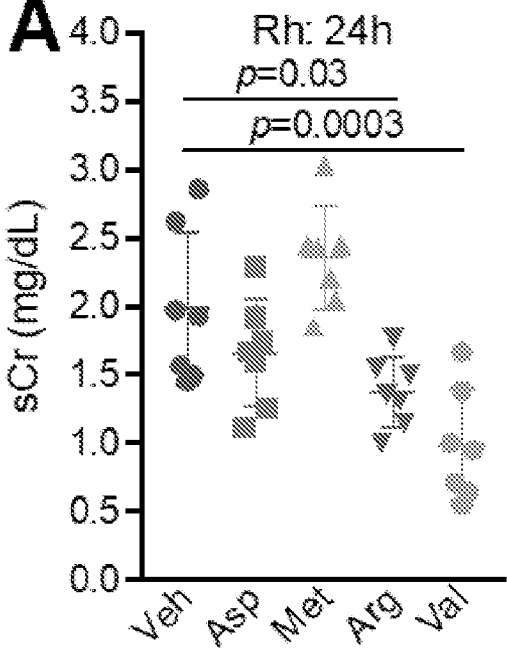
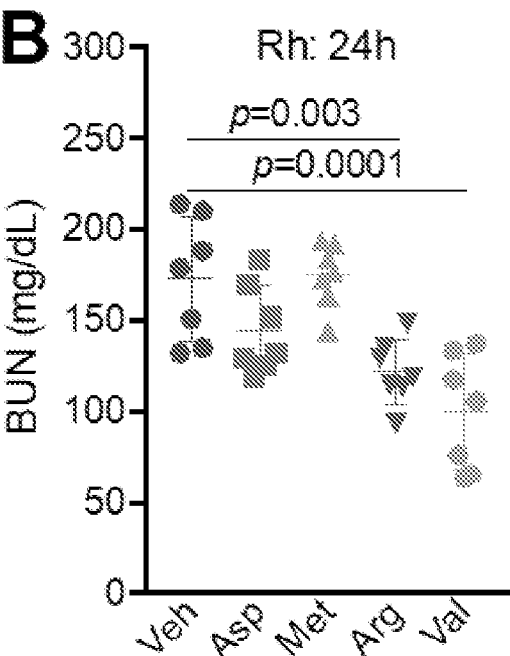
FIGS. 3A-B

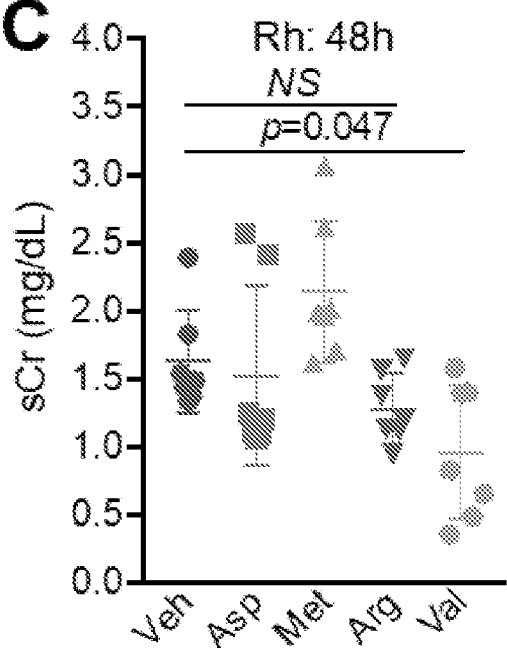
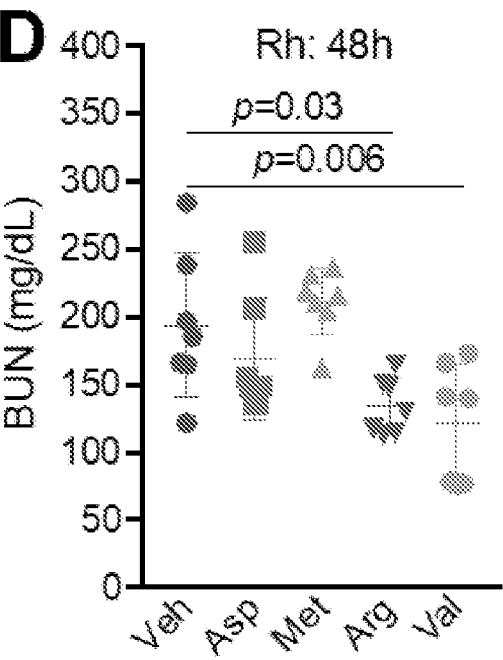
FIGS. 3C-D

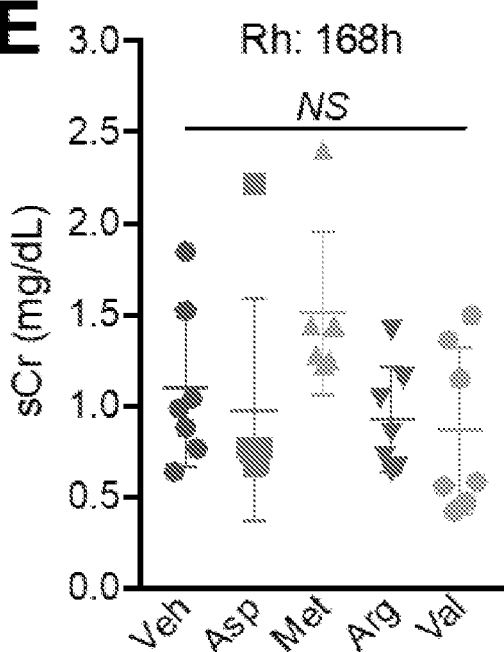
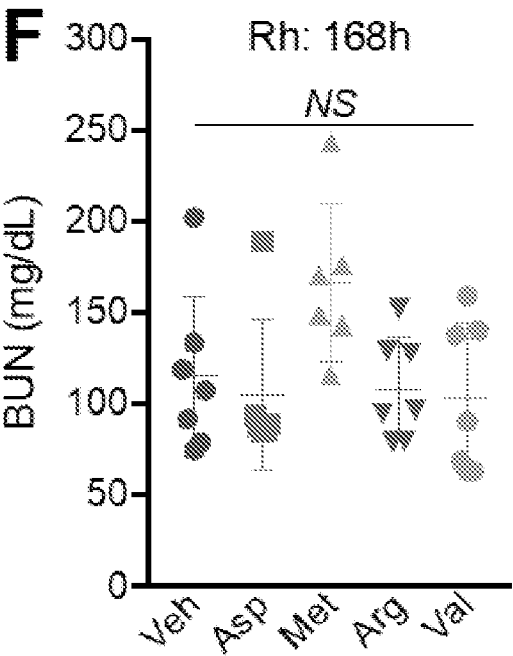
FIGS. 3E-F

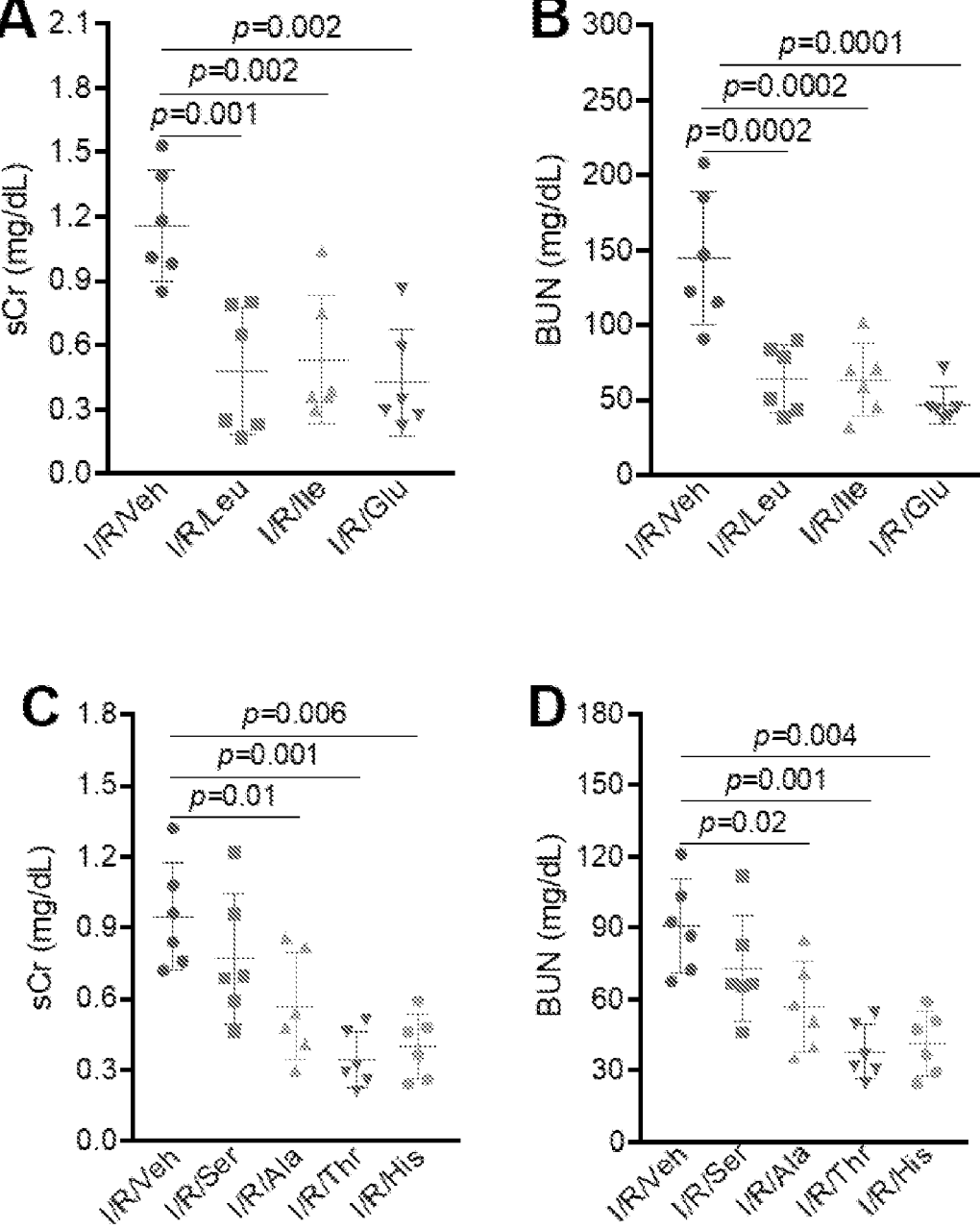
FIGS. 4A-D

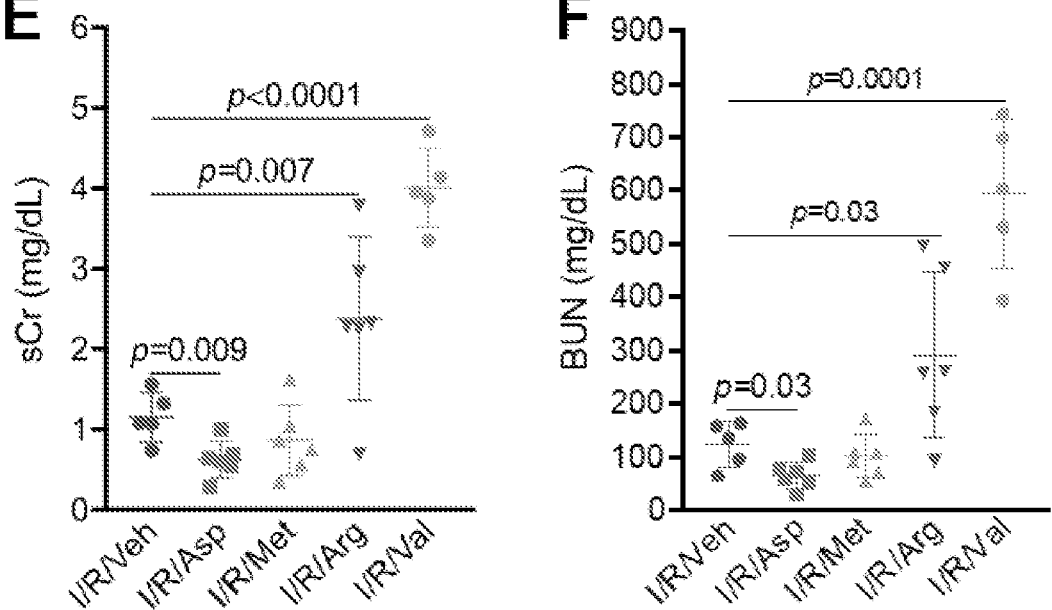
FIGS. 4E-F

REACTIVATION OF MTOR IN ACUTE KIDNEY INJURY (AKI)

This application is a continuation of International Patent Application No. PCT/US2022/012762, filed on Jan. 18, 2022, which claims the benefit of and priority to U.S. Provisional Patent Application No. 63/139,143, filed on Jan. 19, 2021, and U.S. Provisional Patent Application No. 63/144,751, filed on Feb. 2, 2021, the contents of each of which are hereby incorporated by reference in their entireties.

All patents, patent applications and publications cited herein are hereby incorporated by reference in their entirety. The disclosures of these publications in their entireties are hereby incorporated by reference into this application.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

The mammalian Target of Rapamycin (mTOR) pathway regulators cellular, organ and organismal growth and is one of the central nutrient sensing pathways. mTOR is an atypical serine-threonine kinase that nucleates two distinct multi-protein complexes known as mTORC1 and mTORC2.

SUMMARY OF THE INVENTION

In certain aspects the subject matter described herein relates to a method of treating, preventing, or reducing the incidence of Acute Kidney Injury (AKI) in a subject in need thereof, the method comprising administering to the subject via infusion a pharmaceutically effective amount of one or more amino acids.

In some embodiments, the AKI is due to disrupted mTOR signaling. In some embodiments, the disrupted mTOR signaling is due to disrupted endocytosis in the kidney. In some embodiments, the disrupted endocytosis in the kidney is mediated by altered Sphingolipid Transporter 1 (Spns1) activity.

In some embodiments, the AKI is ischemic AKI (iAKI). In some embodiments, the AKI is Rhabdomyolysis (Rh)-induced AKI. In some embodiments, the AKI is ischemia-reperfusion-induced AKI.

In some embodiments, the one or more amino acids is leucine. In some embodiments, the AKI is ischemic AKI. In some embodiments, levels of serum creatinine (sCr) and/or blood urea nitrogen (BUN) are decreased following administration of the one or more amino acids.

In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, the AKI is Rhabdomyolysis (Rh)-induced AKI. In some embodiments, levels of sCr and/or BUN are decreased following administration of the one or more amino acids.

In some embodiments, the one or more amino acid is glutamine. In some embodiments, the one or more amino acid is aspartic acid. In some embodiments, the AKI is ischemia reperfusion (I/R)-induced iAKI. In some embodiments, levels of sCr and/or BUN are decreased following administration of the one or more amino acids.

In some embodiments, the therapeutically effective amount of the one or more amino acids is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, 135 g/kg, about 140 g/kg, about 145 g/kg, or about 150 g/kg. In some embodiments, the one or more amino acids is formulated with at least one excipient suitable for intravenous administration.

In certain aspects, the subject matter described herein relates to a method of treating, preventing, or reducing the incidence of diminished kidney function in a subject in need thereof, the method comprising administering to the subject via infusion a pharmaceutically effective amount of one or more amino acids.

In some embodiments, the diminished kidney function is due to disrupted mTOR signaling. In some embodiments, the disrupted mTOR signaling is due to disrupted endocytosis in the kidney. In some embodiments, the disrupted endocytosis in the kidney is mediated by altered Sphingolipid Transporter 1 (Spns1) activity.

In some embodiments, the diminished kidney function is due to Acute Kidney Injury (AKI). In some embodiments, the AKI is ischemic AKI (iAKI). In some embodiments, the AKI is Rhabdomyolysis (Rh)-induced AKI. In some embodiments, the AKI is ischemia-reperfusion-induced AKI.

In some embodiments, the one or more amino acids is leucine. In some embodiments, levels of serum creatinine (sCr) and/or blood urea nitrogen (BUN) are decreased following administration of the one or more amino acids.

In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, levels of sCr and/or BUN are decreased following administration of the one or more amino acids.

In some embodiments, the one or more amino acid is glutamine. In some embodiments, the one or more amino acid is aspartic acid. In some embodiments, levels of sCr and/or BUN are decreased following administration of the one or more amino acids.

In some embodiments, the therapeutically effective amount of the one or more amino acids is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg. In some embodiments, the one or more amino acids is formulated with at least one excipient suitable for intravenous administration.

In certain aspects, the subject matter described herein relates to a method of treating, preventing, or reducing the incidence of renal failure in a subject in need thereof, the method comprising administering to the subject via infusion a pharmaceutically effective amount of one or more amino acids.

In some embodiments, the renal failure is due to disrupted mTOR signaling. In some embodiments, the disrupted mTOR signaling is due to disrupted endocytosis in the kidney. In some embodiments, the disrupted endocytosis in the kidney is mediated by altered Sphingolipid Transporter 1 (Spns1) activity.

In some embodiments, the renal failure is due to Acute Kidney Injury (AKI). In some embodiments, the AKI is ischemic AKI (iAKI). In some embodiments, the AKI is Rhabdomyolysis (Rh)-induced AKI. In some embodiments, the AKI is ischemia-reperfusion-induced AKI.

In some embodiments, the one or more amino acids is leucine. In some embodiments, levels of serum creatinine (sCr) and/or blood urea nitrogen (BUN) are decreased following administration of the one or more amino acids.

In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, levels of sCr and/or BUN are decreased following administration of the one or more amino acids. In some embodiments, the one or more amino acid is glutamine. In some embodiments, the one or more amino acid is aspartic acid.

In some embodiments, the therapeutically effective amount of the one or more amino acids is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg. In some embodiments, the one or more amino acids is formulated with at least one excipient suitable for intravenous administration.

In certain aspects, the subject matter described herein relates to a method of treating a subject at risk of Acute Kidney Injury (AKI), diminished kidney function due to AKI, or renal failure due to AKI, the method comprising administering to the subject via infusion a pharmaceutically effective amount of one or more amino acids.

In some embodiments, the AKI is due to disrupted mTOR signaling. In some embodiments, the disrupted mTOR signaling is due to disrupted endocytosis in the kidney. In some embodiments, the disrupted endocytosis in the kidney is mediated by altered Sphingolipid Transporter 1 (Spns1) activity.

In some embodiments, the AKI is ischemic AKI (iAKI). In some embodiments, the AKI is Rhabdomyolysis (Rh)-induced AKI. In some embodiments, the AKI is ischemia-reperfusion-induced AKI.

In some embodiments, the one or more amino acids is leucine. In some embodiments, the AKI is ischemic AKI. In some embodiments, levels of serum creatinine (sCr) and/or blood urea nitrogen (BUN) are decreased following administration of the one or more amino acids.

In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, the AKI is Rhabdomyolysis (Rh)-induced AKI. In some embodiments, levels of sCr and/or BUN are decreased following administration of the one or more amino acids.

In some embodiments, the one or more amino acid is glutamine. In some embodiments, the one or more amino acid is aspartic acid. In some embodiments, the AKI is ischemia reperfusion (I/R)-induced iAKI. In some embodiments, levels of sCr and/or BUN are decreased following administration of the one or more amino acids.

In some embodiments, the therapeutically effective amount of the one or more amino acids is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg. In some embodiments, the one or more amino acids is formulated with at least one excipient suitable for intravenous administration.

In certain aspects, the subject matter escribed herein relates to a method of treating, preventing, or reducing the incidence of rhabdomyolysis (Rh)-induced Acute Kidney Injury (AKI) in a subject in need thereof, the method comprising administering to the subject via infusion a pharmaceutically effective amount of one or more amino acids.

In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, levels of sCr and/or BUN are decreased following administration of the one or more amino acids.

In some embodiments, the therapeutically effective amount of the one or more amino acids is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg. In some embodiments, the one or more amino acids is formulated with at least one excipient suitable for intravenous administration.

BRIEF DESCRIPTION OF FIGURES

The patent or application file contains at least one drawing originally in color. To conform to the requirements for PCT patent applications, many of the figures presented herein are black and white representations of images originally created in color.

FIGS. 1A-B show that L-leucine protects from ischemic acute kidney injury (AKI). Serum creatinine (sCr, FIG. 1A) and blood urea nitrogen (BUN, FIG. 1B) levels were assessed in wild type (WT) and nephron-specific Spns1 knockout (Spns1f/f/Six2-Cre) mice.

FIGS. 2A-L show a functional screening of amino acids for the regulation of rhabdomyolysis (Rh)-induced iAKI. FIG. 2A shows sCr levels with vehicle, L-leucine, L-isoleucine or glutamine at 24 hrs post Rh induction. FIG. 2B shows BUN levels with vehicle, L-leucine, L-isoleucine or glutamine at 24 hrs post Rh induction. FIG. 2C shows sCr levels with vehicle, L-leucine, L-isoleucine or glutamine at 48 hrs post Rh induction. FIG. 2D shows BUN levels with vehicle, L-leucine, L-isoleucine or glutamine at 48 hrs post Rh induction. FIG. 2E shows sCr levels with vehicle, L-leucine, L-isoleucine or glutamine at 168 hrs post Rh induction. FIG. 2F shows BUN levels with vehicle, L-leucine, L-isoleucine or glutamine at 168 hrs post Rh induction. FIG. 2G shows sCr levels with vehicle, L-serine, alanine, threonine, or histidine at 24 hrs post Rh induction. FIG. 2H shows BUN levels with vehicle, L-serine, alanine, threonine, or histidine at 24 hrs post Rh induction. FIG. 2I shows sCr levels with vehicle, L-serine, alanine, threonine or histidine at 48 hrs post Rh induction. FIG. 2J shows BUN levels with vehicle, L-serine, alanine, threonine or histidine at 48 hrs post Rh induction. FIG. 2K shows sCr levels with vehicle, L-serine, alanine, threonine or histidine at 168 hrs post Rh induction. FIG. 2L shows BUN levels with vehicle, L-serine, alanine, threonine or histidine at 168 hrs post Rh induction.

FIGS. 3A-F show a functional screening of amino acids for the regulation of rhabdomyolysis (Rh)-induced iAKI. FIG. 3A shows sCr levels with vehicle, L-aspartic acid, L-methionine, L-arginine or L-valine at 24 hrs post Rh induction. FIG. 3B shows BUN levels with vehicle, L-aspartic acid, L-methionine, L-arginine or L-valine at 24 hrs post Rh induction. FIG. 3C shows sCr levels with vehicle, L-aspartic acid, L-methionine, L-arginine or L-valine at 48 hrs post Rh induction. FIG. 3D shows BUN levels with vehicle, L-aspartic acid, L-methionine, L-arginine or L-valine at 48 hrs post Rh induction. FIG. 3E shows sCr levels with vehicle, L-aspartic acid, L-methionine, L-arginine or L-valine at 168 hrs post Rh induction. FIG. 3F shows BUN levels with vehicle, L-aspartic acid, L-methionine, L-arginine or L-valine at 168 hrs post Rh induction.

FIGS. 4A-F show functional screening of amino acids for the regulation of ischemia reperfusion (I/R)-induced iAKI. FIG. 4A shows serum creatinine (sCr) levels following vehicle, L-leucine (Leu), L-isoleucine (Ile), or L-glutamine (Glu) administration. FIG. 4B shows blood urea nitrogen (BUN) levels following vehicle, L-leucine (Leu), L-isoleucine (Ile), or L-glutamine (Glu) administration. FIG. 4C shows sCr levels following vehicle, L-serine (Ser), L-alanine (Ala), L-threonine (Thr), or L-histidine (His) administration. FIG. 4D shows BUN levels following vehicle, L-serine (Ser), L-alanine (Ala), L-threonine (Thr), or L-histidine (His) administration. FIG. 4E shows sCr levels following vehicle, L-aspartic acid (Asp), L-methionine (Met), L-arginine (Arg), or L-valine (Val) administration. FIG. 4F shows BUN levels following vehicle, L-aspartic acid (Asp), L-methionine (Met), L-arginine (Arg), or L-valine (Val) administration. sCr and BUN levels were analyzed after reperfusion for 48 hours.

DETAILED DESCRIPTION OF THE INVENTION

Definitions

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the term "subject" refers to a vertebrate animal. In one embodiment, the subject is a mammal or a mammalian species. In one embodiment, the subject is a human. In one embodiment, the subject is a healthy human adult. In other embodiments, the subject is a non-human vertebrate animal, including, without limitation, non-human primates, laboratory animals, livestock, racehorses, domesticated animals, and non-domesticated animals. In one embodiment, the term "human subjects" means a population of healthy human adults.

As used herein, the term "patient" refers to a human or animal.

The term "mammal" includes, but is not limited to, a human, mouse, rat, guinea pig, dog, cat, horse, cow, pig, or non-human primate, such as a monkey, chimpanzee, baboon or rhesus. In one embodiment, the mammal is a human.

As used herein, the term "therapeutically effective" includes prophylaxis, as well as treatment of a subject having suspected of having a viral infection.

Non-Limiting Embodiments of the Subject Matter

In certain aspects the subject matter described herein relates to a method of treating, preventing, or reducing the incidence of Acute Kidney Injury (AKI) in a subject in need thereof, the method comprising administering to the subject via infusion a pharmaceutically effective amount of one or more amino acids.

In some embodiments, the AKI is due to disrupted mTOR signaling. In some embodiments, the disrupted mTOR signaling is due to disrupted endocytosis in the kidney. In some embodiments, the disrupted endocytosis in the kidney is mediated by altered Sphingolipid Transporter 1 (Spns1) activity.

In some embodiments, the AKI is ischemic AKI (iAKI). In some embodiments, the AKI is Rhabdomyolysis (Rh)-induced AKI. In some embodiments, the AKI is ischemia-reperfusion-induced AKI.

In some embodiments, the one or more amino acids is leucine. In some embodiments, the AKI is ischemic AKI. In some embodiments, levels of serum creatinine (sCr) and/or blood urea nitrogen (BUN) are decreased following administration of the one or more amino acids.

In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, the AKI is Rhabdomyolysis (Rh)-induced AKI. In some embodiments, levels of sCr and/or BUN are decreased following administration of the one or more amino acids.

In some embodiments, the one or more amino acid is glutamine. In some embodiments, the one or more amino acid is aspartic acid. In some embodiments, the AKI is ischemia reperfusion (I/R)-induced iAKI. In some embodiments, levels of sCr and/or BUN are decreased following administration of the one or more amino acids.

In some embodiments, the therapeutically effective amount of the one or more amino acids is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg. In some embodiments, the one or more amino acids is formulated with at least one excipient suitable for intravenous administration.

In certain aspects, the subject matter described herein relates to a method of treating, preventing, or reducing the incidence of diminished kidney function in a subject in need thereof, the method comprising administering to the subject via infusion a pharmaceutically effective amount of one or more amino acids.

In some embodiments, the diminished kidney function is due to disrupted mTOR signaling. In some embodiments, the disrupted mTOR signaling is due to disrupted endocytosis in the kidney. In some embodiments, the disrupted endocytosis in the kidney is mediated by altered Sphingolipid Transporter 1 (Spns1) activity.

In some embodiments, the diminished kidney function is due to Acute Kidney Injury (AKI). In some embodiments, the AKI is ischemic AKI (iAKI). In some embodiments, the AKI is Rhabdomyolysis (Rh)-induced AKI. In some embodiments, the AKI is ischemia-reperfusion-induced AKI.

In some embodiments, the one or more amino acids is leucine. In some embodiments, levels of serum creatinine (sCr) and/or blood urea nitrogen (BUN) are decreased following administration of the one or more amino acids.

In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, levels of sCr and/or BUN are decreased following administration of the one or more amino acids.

In some embodiments, the one or more amino acid is glutamine. In some embodiments, the one or more amino acid is aspartic acid. In some embodiments, levels of sCr and/or BUN are decreased following administration of the one or more amino acids.

In some embodiments, the therapeutically effective amount of the one or more amino acids is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg. In some embodiments, the one or more amino acids is formulated with at least one excipient suitable for intravenous administration.

In certain aspects, the subject matter described herein relates to a method of treating, preventing, or reducing the incidence of renal failure in a subject in need thereof, the method comprising administering to the subject via infusion a pharmaceutically effective amount of one or more amino acids.

In some embodiments, the renal failure is due to disrupted mTOR signaling. In some embodiments, the disrupted mTOR signaling is due to disrupted endocytosis in the kidney. In some embodiments, the disrupted endocytosis in the kidney is mediated by altered Sphingolipid Transporter 1 (Spns1) activity.

In some embodiments, the renal failure is due to Acute Kidney Injury (AKI). In some embodiments, the AKI is ischemic AKI (iAKI). In some embodiments, the AKI is Rhabdomyolysis (Rh)-induced AKI. In some embodiments, the AKI is ischemia-reperfusion-induced AKI.

In some embodiments, the one or more amino acids is leucine. In some embodiments, levels of serum creatinine (sCr) and/or blood urea nitrogen (BUN) are decreased following administration of the one or more amino acids.

In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, levels of sCr and/or BUN are decreased following administration of the one or more amino acids. In some embodiments, the one or more amino acid is glutamine. In some embodiments, the one or more amino acid is aspartic acid.

In some embodiments, the therapeutically effective amount of the one or more amino acids is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg. In some embodiments, the one or more amino acids is formulated with at least one excipient suitable for intravenous administration.

In certain aspects, the subject matter described herein relates to a method of treating a subject at risk of Acute Kidney Injury (AKI), diminished kidney function due to AKI, or renal failure due to AKI, the method comprising administering to the subject via infusion a pharmaceutically effective amount of one or more amino acids.

In some embodiments, the AKI is due to disrupted mTOR signaling. In some embodiments, the disrupted mTOR signaling is due to disrupted endocytosis in the kidney. In some embodiments, the disrupted endocytosis in the kidney is mediated by altered Sphingolipid Transporter 1 (Spns1) activity.

In some embodiments, the AKI is ischemic AKI (iAKI). In some embodiments, the AKI is Rhabdomyolysis (Rh)-induced AKI. In some embodiments, the AKI is ischemia-reperfusion-induced AKI.

In some embodiments, the one or more amino acids is leucine. In some embodiments, the AKI is ischemic AKI. In some embodiments, levels of serum creatinine (sCr) and/or blood urea nitrogen (BUN) are decreased following administration of the one or more amino acids.

In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, the AKI is Rhabdomyolysis (Rh)-induced AKI. In some embodiments, levels of sCr and/or BUN are decreased following administration of the one or more amino acids.

In some embodiments, the one or more amino acid is glutamine. In some embodiments, the one or more amino acid is aspartic acid. In some embodiments, the AKI is ischemia reperfusion (I/R)-induced iAKI. In some embodiments, levels of sCr and/or BUN are decreased following administration of the one or more amino acids.

In some embodiments, the therapeutically effective amount of the one or more amino acids is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg. In some embodiments, the one or more amino acids is formulated with at least one excipient suitable for intravenous administration.

In certain aspects, the subject matter escribed herein relates to a method of treating, preventing, or reducing the incidence of rhabdomyolysis (Rh)-induced Acute Kidney Injury (AKI) in a subject in need thereof, the method comprising administering to the subject via infusion a pharmaceutically effective amount of one or more amino acids.

In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, levels of sCr and/or BUN are decreased following administration of the one or more amino acids.

In some embodiments, the therapeutically effective amount of the one or more amino acids is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg. In some embodiments, the one or more amino acids is formulated with at least one excipient suitable for intravenous administration.

Method of Treating Acute Kidney Injury

Acute kidney injury (AKI) is loss of kidney function typically caused by reduced blood flow to the kidneys. AKI is of particular concern as it occurs in approximately 17% of patients in intensive care units (ICUs), and has a high mortality rate of 23% in this patient population. Currently available treatments focus on mitigating the symptoms of AKI with varied efficacy.

AKI is characterized by rapid loss of the excretory function of the kidney. AKI is diagnosed by the accumulation of end products of nitrogen metabolism (urea and creatinine) and/or decreased urine output. There are no therapies available that can attenuate AKI or expedite recovery; thus, treatment is primarily supportive. Patients are given renal replacement therapy if AKI is severe and biochemical or volume-related, or if there are concerns for uraemic-toxaemia-related complications. Survivors of AKI can recover to dialysis independence. However, patients who have had AKI once are at increased risk of subsequent chronic kidney disease.

In some embodiments, the subject matter described herein relates to methods of treating AKI in a subject in need thereof. In some embodiments, the treatment comprises administering to the subject via infusion a pharmaceutically effective amount of one or more amino acids. In some embodiments, the AKI is due to disrupted mTOR signaling. In some embodiments, the disrupted mTOR signaling is due to disrupted endocytosis in the kidney. In some embodiments, the disrupted endocytosis in the kidney is mediated by altered Sphingolipid Transporter 1 (Spns1) activity. In some, embodiments, the AKI is due to decreased oxygen supply (e.g. ischemic AKI). In some embodiments, the AKI is Rhabdomyolysis (Rh)-induced AKI. In some embodiments, the AKI is ischemia-reperfusion-induced AKI.

In some embodiments, the one or more amino acids administered to the subject is leucine. In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, the one or more amino acid is glutamine. In some embodiments, the one or more amino acid is aspartic acid. In some embodiments, levels of serum creatinine (sCr) and/or blood urea nitrogen (BUN) are decreased following administration of the one or more amino acids.

In some embodiments, the one or more amino acids is administered to the subject in a therapeutically effective amount. In some embodiments, the therapeutically effective amount is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg.

In some embodiments, the subject matter described herein relates to the identification of a functional relationship between mammalian target of rapamycin (mTOR) and AKI. In some embodiments the subject matter described herein relates to the function of the ion channel Spns1. In some embodiments, Spns1 dysfunction disrupts endocytosis in the kidney due to a defect in mTOR signaling. One or more Amino acid infusions can rescue this defect. Dysfunctional mTOR signaling results in impaired endocytosis in the kidney via altered ion channel activity. Infusions of amino acids can also restore mTOR function and rescue the kidney from ischemic AKI. As such, targeting dysfunctional mTOR signaling with amino acids may serve as an effective treatment regimen for AKI. The amino acid infusion can be a one-time administration of one or more amino acids or it can be a continuous treatment with one or more amino acids over a longer period of time. The period of time can be three days, five days, one week, two weeks, three weeks, or a life-time dependency on amino acid infusions.

Activation of mTORC1 by Amino Acids

Nutrient sensing by cells is crucial for their survival and it can be mediated by mTOR complex 1 (mTORC1), which senses amino acids to control cell growth, metabolism, autophagy, and other cellular processes. mTORC1 dysfunction is associated with many human diseases, including cancer, obesity, type 2 diabetes, neurodegeneration, and metabolic disorders. Amino acid availability promotes mTORC1 lysosomal localization, where it is subsequently activated by Rheb downstream of growth factors.

All amino acids except for glycine are stereoisomers: L- and D-mirror images of the their structure. The amino acids making up proteins in our bodies are all L-amino acids. L-amino acids are essential for life because they provide the building blocks of proteins in all kingdoms of life. In some embodiments, each amino acid disclosed herein is synonymous and used interchangeably with the L-stereoisomer of that amino acid. The amino acids alanine, arginine, asparagine, glutamine, histidine, leucine, methionine, serine, threonine, and valine activate mTORC1 in mouse embryonic fibroblast (MEF) and human embryonic kidney 293A (HEK293A) cells. Cysteine activates mTORC1 in MEF cells but not in HEK293A cells. This activation is shown by immunoblotting for the phosphorylation of mTORC1's substrate, S6K1, at threonine 389 (pS6K1). These amino acids also promote mTORC1's lysosomal localization. v-ATPase and lysosomal function are required for the amino acids to activate mTORC1. v-ATPase is responsible for acidifying the lysosome and maintaining lysosomal function.

Rag GTPases link amino acid signaling to mTORC1 activation at the lysosome. This is one pathway of mTORC1 activation by amino acids. RagA or RagB forms a heterodimer with RagC or RagD, and dimerization is essential for Rag GTPase protein stability and mTORC1 activation. The guanine nucleotide loading of the Rag GTPases is important for their physiological function, where GTP-bound RagA or RagB interacts with the mTORC1 component Raptor at the lysosome. RagC or RagD GDP-bound forms a heterodimer with the GTP-bound RagA or RagB. Other components have been also reported to be involved in the Rag GTPase signaling cascade to mTORC1.

Alanine, arginine, histidine, leucine, methionine, serine, threonine, and valine signal to mTORC1 through the Rag GTPase-dependent signaling pathway. The leucine and arginine sensors have been identified as Sestrin2 and CASTOR1, respectively, which are proteins located upstream of the Rag GTPases and are required for mTORC1 activation. Additionally, SAMTOR is an S-adenosylmethionine sensor that couples methionine to mTORC1 in a Rag-dependent manner.

In contrast, glutamine activates mTORC1 through a Rag GTPase-independent mechanism that requires the ADP-ribosylation factor 1 (Arf1). Like glutamine, asparagine signals to mTORC1 through Arf1 in the absence of the Rag GTPases. Glutamine and asparagine activation of mTORC1 in Rag GTPase KO cells is comparable with that in wild type cells. This Gln-TORC1 pathway is conserved in yeast, where VPS34 and Pib2 are thought to be involved. However, the Gln sensor and other components involved in the Rag-independent pathway in mammals have yet to be discovered.

Both the Rag-dependent and Rag-independent pathways required the lysosome and lysosomal function for mTORC1 activation.

Additionally, in the absence of Rag GTPases, glutamine and asparagine are still able to induce lysosomal localization of mTORC1. Stimulation of HEK293A cells with saturating concentrations of either glutamine or asparagine leads to mTORC1 activation. Interestingly, the simultaneous addition of saturating concentrations of both glutamine and asparagine further increased mTORC1 activity, suggesting that there is a synergistic relationship between the two amino acids. This synergy also suggests that there are different sensors or modes of action utilized by glutamine and asparagine to activate mTORC1.

Glutamine and asparagine signaling to mTORC1 in the absence of the Rag GTPases requires the function of Arf1. Treatment with brefeldin A (BFA), an Arf1 guanine exchange factor inhibitor, inhibits both glutamine and asparagine-induced mTORC1 activation in both wild type and Rag depleted MEFs. Additionally, this treatment impairs lysosomal localization of mTORC1 induced by glutamine and asparagine. Glutamine and asparagine fail to signal to mTORC1 in cells exposed to siRNA to Arf1.

In some embodiments the subject matter described herein relates to targeting dysfunctional mTOR signaling in a subject in need thereof by administering one or more amino acids as a treatment for AKI. In some embodiments, the one or more amino acids administered to the subject is leucine. In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, the one or more amino acid is glutamine. In some embodiments, the one or more amino acid is aspartic acid. In some embodiments, the one or more amino acids administered to the subject is L-leucine. In some embodiments, the one or more amino acids is L-isoleucine. In some embodiments, the one or more amino acids is L-threonine. In some embodiments, the one or more amino acids is L-histidine. In some embodiments, the one or more amino acids is L-valine. In some embodiments, the one or more amino acids is L-arginine. In some embodiments, the one or more amino acid is L-glutamine. In some embodiments, the one or more amino acid is L-aspartic acid. In some embodiments, levels of serum creatinine (sCr) and/or blood urea nitrogen (BUN) are decreased following administration of the one or more amino acids.

In some embodiments, the one or more amino acids is administered to the subject in a therapeutically effective amount. In some embodiments, the therapeutically effective amount is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg.

Rhabdomyolysis

Rhabdomyolysis (Rh) is a syndrome caused by direct or indirect muscle injury where death of muscle fibers releases of their contents into the bloodstream. Rhabdomyolysis can lead to serious complications such as renal (kidney) failure—Rhabdomyolysis-induced acute kidney injury. During failure the kidneys cannot remove waste and concentrated urine from the body. In rare cases, rhabdomyolysis can lead to death, however, this is preventable with prompt treatment.

In some embodiments the subject matter described herein relates to treating Rhabdomyolysis-induced acute kidney injury in a subject in need thereof. In some embodiments, the treating comprises administering to the subject one or more amino acids. In some embodiments, the one or more amino acids administered to the subject is leucine. In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, the one or more amino acid is glutamine. In some embodiments, the one or more amino acid is aspartic acid. In some embodiments, the one or more amino acids administered to the subject is L-leucine. In some embodiments, the one or more amino acids is L-isoleucine. In some embodiments, the one or more amino acids is L-threonine. In some embodiments, the one or more amino acids is L-histidine. In some embodiments, the one or more amino acids is L-valine. In some embodiments, the one or more amino acids is L-arginine. In some embodiments, the one or more amino acid is L-glutamine. In some embodiments, the one or more amino acid is L-aspartic acid. In some embodiments, levels of serum creatinine (sCr) and/or blood urea nitrogen (BUN) are decreased following administration of the one or more amino acids.

In some embodiments, the one or more amino acids is administered to the subject in a therapeutically effective amount. In some embodiments, the therapeutically effective amount is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg.

Ischemic AKI

Ischemia is the leading cause of AKI. During ischemia the blood flow and oxygen supply is reduced in a part of the body such as the kidney. The blood flow can be restricted to the organ itself or to particular areas of the organ. This affects the cellular metabolism in the affected area. Ischemia reperfusion injury is caused when blood supply returns to a previously ischemic tissue.

In some embodiments the subject matter described herein relates to treating ischemic acute kidney injury in a subject in need thereof. In some embodiments, the treating comprises administering to the subject one or more amino acids. In some embodiments, the one or more amino acids administered to the subject is leucine. In some embodiments, the one or more amino acids is isoleucine. In some embodiments, the one or more amino acids is threonine. In some embodiments, the one or more amino acids is histidine. In some embodiments, the one or more amino acids is valine. In some embodiments, the one or more amino acids is arginine. In some embodiments, the one or more amino acid is glutamine. In some embodiments, the one or more amino acid is aspartic acid. In some embodiments, the one or more amino acids administered to the subject is L-leucine. In some embodiments, the one or more amino acids is L-isoleucine. In some embodiments, the one or more amino acids is L-threonine. In some embodiments, the one or more amino acids is L-histidine. In some embodiments, the one or more amino acids is L-valine. In some embodiments, the one or more amino acids is L-arginine. In some embodiments, the one or more amino acid is L-glutamine. In some embodiments, the one or more amino acid is L-aspartic acid. In some embodiments, levels of serum creatinine (sCr) and/or blood urea nitrogen (BUN) are decreased following administration of the one or more amino acids.

In some embodiments, the one or more amino acids is administered to the subject in a therapeutically effective amount. In some embodiments, the therapeutically effective amount is about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, or about 150 g/kg.

Administration of Amino Acids

In some embodiments, the subject matter described herein relates to treating an Acute Kidney Injury (AKI) by administering a pharmaceutically effective amount of one or more amino acids. In some embodiments, the one or more amino acids is administered via an infusion. In some embodiments, the infusion is an intravenous (IV) infusion. Intravenous drug administration is the most common parental route of medication administration. This route has the benefit of bypassing the first-pass metabolism of drugs in the liver. Peripheral veins provide easy access to the circulatory system because they are superficially located on the skin. In some embodiments, the one or more amino acids is administered intramuscularly. In some embodiments, the one or more amino acids is administered through the enteral route. In some embodiments, the one or more amino acids is administered orally. In some embodiments, the one or more amino acids is administered sublingually or buccally. In some embodiments, the one or more amino acids is administered subcutaneously. In some embodiments, the one or more amino acids is administered intranasally. In some embodiments, the one or more amino acids is administered via inhalation.

In some embodiments, the therapeutically effective amount is about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 1 g/kg, about 5 g/kg, about 10 g/kg, about 15 g/kg, about 20 g/kg, about 25 g/kg, about 30 g/kg, about 35 g/kg, about 40 g/kg, about 45 g/kg, about 50 g/kg, about 55 g/kg, about 60 g/kg, about 65 g/kg, about 70 g/kg, about 75 g/kg, about 80 g/kg, about 85 g/kg, about 90 g/kg, about 95 g/kg, about 100 g/kg, about 105 g/kg, about 110 g/kg, about 115 g/kg, about 120 g/kg, about 125 g/kg, about 130 g/kg, about 135 g/kg, about 140 g/kg, about 145 g/kg, about 150 g/kg, about 160 g/kg, about 170 g/kg, about 180 g/kg about 190 g/kg, about 200 g/kg, about 210 g/kg, about 220 g/kg, about 230 g/kg, about 240 g/kg, about 250 g/kg, about 260 g/kg, about 270 g/kg, about 280 g/kg, about 290 g/kg, about 300 g/kg.

In some embodiments, the one or more amino acids is formulated with at least one excipient suitable for intravenous administration. In some embodiments, the one or more excipient is any excipient known in the art to be used in intravenous formulation of proteins, peptides, or amino acids or a combination thereof. In some embodiments, the excipient is a dextrose solution or saline, at a pharmaceutically acceptable concentration. In some embodiments, the one or more excipient is a solubilizing agent. In some embodiments the excipient is a cyclodextrin. In some embodiments, the one or more excipient is a stabilizing agent. In some embodiments, the excipient is one or more pH-buffering salts. In some embodiments, the composition comprising the one or more amino acids can be administered to a patient via an i.v. bag. In some embodiments, the one or more amino acids are lyophilized. This process is also known as freeze-drying is a dehydration process to remove the liquid from a material.

Serum Creatinine (sCr) and Blood Urea Nitrogen (BUN) Indicators

The serum creatinine test measures the amount of creatinine in a subject's blood. Creatinine is a waste product produced from the normal wear and tear on body muscles. Creatinine waste is filtered out of the blood by the kidneys and leave the body in urine. If the kidneys are not working properly, such as during AKI, then the amount of creatinine in the blood can increase. Therefore, the amount of creatinine in the blood (serum creatinine, or sCr) is an indicator of kidney function. A creatinine urine test can also be used to measure creatinine in the urine. This urine test can also be used to assess kidney function. In some embodiments, a sCr level of greater than 1.2 mg/dL for women and greater than 1.4 mg/dL for men may be an indicator of kidney dysfunction, such as AKI. However, the "normal" creatinine level can depend on age, race, gender, and body size. In some embodiments, the subject matter described herein relates to the use of sCr levels as an indicator of kidney function or dysfunction.

Blood urea nitrogen (BUN) is a blood test which can also indicate kidney dysfunction. Urea nitrogen comes from the breakdown of protein in food. Normally, nitrogen in the blood binds to other wastes that are filtered by the kidneys and leave the body in the urine. The BUN test measures the amount of urea nitrogen in the blood. If the subject is experiencing kidney dysfunction, such as AKI, the amount of urea nitrogen in the blood can be higher than the amount in a subject with healthy kidneys. In some embodiments, a normal human BUN level is between 7 mg/dL and 20 mg/dL. In some embodiments, the subject matter described herein relates to the use of BUN levels as an indicator of kidney function or dysfunction.

EXAMPLES

Example 1

FIGS. 1A-B show that L-leucine administration protected from ischemic acute kidney injury (AKI). L-leucine (75 mg/kg) was intraperitoneally administered into wild type (WT) and nephron-specific Spns1 knockout (Spns1f/f/Six2-Cre) mice 1 hour prior to initiating ischemic AKI. The left kidney was then removed. Ischemia/reperfusion (IR) was performed by clamping the renal artery of the right kidney for 25 min of ischemia followed by 48 hours of reperfusion. Serum creatinine (sCr, FIG. 1A) and blood urea nitrogen (BUN, FIG. 1B) levels were increased in Spns1f/f/Six2-Cre mice compared with WT vehicle-injected IR AKI mice Both indicators were markedly reduced by leucine treatment in both WT and Spns1f/f/Six2-Cre IR AKI mice. n=4-7.

FIGS. 2A-L show a functional screening of amino acids for the regulation of rhabdomyolysis (Rh)-induced iAKI. Rh was incurred by intramuscularly injecting 50% glycerol (6 ml/kg), and renal functions were analyzed by quantitating serum creatinine (sCr) and blood urea nitrogen (BUN) after 24, 48 and 168 hours. A-F. L-leucine, L-isoleucine or glutamine (75 mg/kg) were intraperitoneally administered into wild type C57BL6 mice at 1 hour prior to injury incurrence.

It was observed that sCr and BUN were reduced at 24 hours (FIGS. 2A, B) in isoleucine-treated rhabdomyolysis mice, but were increased at 48 hours in leucine-treated mice (FIGS. 2C, D) when compared with vehicle (Veh)-treated counterparts (n=7). This result indicates that isoleucine protects from Rh-induced AKI at 24 h, but leucine demonstrated the opposite effects at 48 h. Glutamine had no significant effects. FIG. 2G-L. L-serine, alanine, threonine, or histidine were intraperitoneally administered into wild type C57BL6 mice at 1 hour prior to injury incurrence and then every 8 hours thereafter. It was observed that threonine reduces sCr and BUN at 24 h and histidine reduces sCr and BUN at 24 h and 48 h when compared with Veh Rh mice. Therefore, threonine and histidine protected from Rh-induced iAKI. No effects of these amino acids were observed at 168 h.

FIGS. 3A-F show a functional screening of L-aspartic acid, L-methionine, L-arginine or L-valine for the regulation of rhabdomyolysis (Rh)-induced iAKI. Rh was incurred by intramuscularly injecting 50% glycerol (6 ml/kg), and renal functions were analyzed by quantitating serum creatinine (sCr) and blood urea nitrogen (BUN) after 24, 48 and 168 hours. FIGS. 3A-F. L-aspartic acid, L-methionine, L-arginine or L-valine (75 mg/kg) were intraperitoneally administered into wild type C57BL6 mice at 1 hour prior to injury incurrence and then every 8 hours for a total of 5 doses.

It was observed that sCr and BUN were reduced at 24 hours (FIGS. 3A, B) in L-arginine and L-valine-treated rhabdomyolysis mice and at 48 hours (FIGS. 3C, D) in L-valine-treated rhabdomyolysis mice when compared with vehicle (Veh)-treated counterparts (n=7). This indicates that L-valine protected from Rh-induced AKI at 24 h and 48 h, but L-arginine only protected from Rh-induced AKI at 24 h. No effects of these amino acids were observed at 168 h.

Example 2

FIGS. 4A-F show functional screening of amino acids for the regulation of ischemia reperfusion (I/R)-induced iAKI. Ischemia was incurred by clamping renal artery of the left kidney for 25 min while the right kidney was removed prior to clamping. Renal functions were analyzed by quantitating serum creatinine (sCr) and blood urea nitrogen (BUN) after the reperfusion for 48 hours. FIGS. 4A-F. L-leucine (Leu), L-isoleucine (Ile), L-glutamine (Glu), L-serine (Ser), L-alanine (Ala), L-threonine (Thr), L-histidine (His), L-aspartic acid (Asp), L-methionine (Met), L-arginine (Arg) or L-valine (Val; 75 mg/kg) were intraperitoneally administered into wild type C57B/L6 mice 1 hour prior to the induction of ischemic and every 8 hours afterwards.

sCr and BUN were reduced at 48 hours in L-leucine (FIGS. 4A, B), L-isoleucine (A, B), L-glutamine (A, B), L-threonine (C, D), L-histidine (C, D) or L-aspartic acid (FIGS. 4E, F)-treated ischemic mice when compared with vehicle (Veh)-treated counterparts (n=5-6), indicating that L-leucine, L-isoleucine, L-glutamine, L-threonine, L-histidine and L-aspartic acid protected from I/R-induced AKI at 48 h. In contrast, treatment with L-arginine (FIG. 4E, F) or L-valine (FIGS. 4E, F) elevated sCr and BUN at 48 h when compared with Veh-treated counterparts, indicating that these two amino acids worsened FR-induced AKI. Neither L-serine (FIGS. 4A, B), L-alanine (FIGS. 4A, B) nor L-me-thionine (FIGS. 4C, D) had significant impacts on I/R-AKI.

What is claimed is:

1. A method of treating, preventing, or reducing incidence of Acute Kidney Injury (AKI) in a subject in need thereof, the method comprising administering to the subject a pharmaceutically effective amount of one or more amino acids, wherein the subject has disrupted mTOR signaling, and wherein the one or more amino acids is selected from leucine, isoleucine, threonine, histidine, valine, arginine, glutamine, aspartic acid, or a combination thereof.

2. The method of claim 1, comprising administering to the subject the pharmaceutically effective amount of the one or more amino acids via infusion.

3. The method of claim 1, wherein before administration of the pharmaceutically effective amount of one or more amino acids, endocytosis is disrupted in a kidney of the subject.

4. The method of claim 3, wherein the disrupted endo-cytosis in the kidney is associated with the presence of altered Sphingolipid Transporter 1 (Spns1) activity in the subject.

5. The method of claim 1, wherein the AKI is Rhabdomy-olysis (Rh)-induced AKI.

6. The method of claim 1, wherein the AKI is ischemic AKI (iAKI).

7. The method of claim 6, wherein the iAKI is ischemia-reperfusion (I/R)-induced iAKI.

8. The method of claim 1, wherein the AKI is Rh-induced AKI and the one or more amino acids is selected from isoleucine, threonine, arginine, valine, histidine, or a com-bination thereof.

9. The method of claim 1, wherein the AKI is I/R-induced iAKI and the one or more amino acids is selected from leucine, isoleucine, glutamine, threonine, histidine, aspartic acid, or a combination thereof.

10. The method of claim 1, wherein a level of serum creatinine (sCr) or a level of blood urea nitrogen (BUN) is decreased in the subject following the administration of the pharmaceutically effective amount of the one or more amino acids.

11. The method of claim 1, wherein the one or more amino acids is formulated with at least one excipient suitable for intravenous administration.

12. A method of treating, preventing, or reducing a diminished kidney function or a renal failure in a subject in need thereof, the method comprising administering to the subject a pharmaceutically effective amount of one or more amino acids, wherein the diminished kidney function or renal failure of the subject is due to AKI and wherein the subject has disrupted mTOR signaling, and wherein the one or more amino acids is selected from leucine, isoleucine, threonine, histidine, valine, arginine, glutamine, aspartic acid, or a combination thereof.

13. The method of claim 12, comprising administering to the subject the pharmaceutically effective amount of the one or more amino acids via infusion.

14. The method of claim 12, wherein before administra-tion of the pharmaceutically effective amount of one or more amino acids, endocytosis is disrupted in a kidney of the subject.

15. The method of claim 14, wherein the disrupted endocytosis in the kidney is associated with the presence of altered Sphingolipid Transporter 1 (Spns1) activity in the subject.

16. The method of claim 12, wherein the AKI is Rhab-domyolysis (Rh)-induced AKI.

17. The method of claim 12, wherein the AKI is ischemic AKI (iAKI).

18. The method of claim 17, wherein the iAKI is isch-emia-reperfusion (I/R)-induced iAKI.

19. The method of claim 12, wherein the AKI is Rh-induced AKI and the one or more amino acids is selected from isoleucine, threonine, arginine, valine, histidine, or a combination thereof.

20. The method of claim 12, wherein the AKI is I/R-induced iAKI and the one or more amino acids is selected from leucine, isoleucine, glutamine, threonine, histidine, aspartic acid, or a combination thereof.

21. The method of claim 12, wherein a level of serum creatinine (sCr) or a level of blood urea nitrogen (BUN) is decreased in the subject following the administration of the pharmaceutically effective amount of the one or more amino acids.

* * * * *